United States Patent

Nagasawa et al.

(10) Patent No.: US 7,632,424 B2
(45) Date of Patent: Dec. 15, 2009

(54) METHOD FOR INHIBITING THE DISCOLORATION OF METHYLENEBISANILINE COMPOUNDS

(75) Inventors: Mato Nagasawa, Shizuoka (JP); Naoya Atsumi, Shizuoka (JP); Hirofumi Ichikawa, Osaka (JP)

(73) Assignee: Ihara Chemical Industry Co., Ltd. (JP)

( * ) Notice: Subject to any disclaimer, the term of this patent is extended or adjusted under 35 U.S.C. 154(b) by 669 days.

(21) Appl. No.: 10/583,722

(22) PCT Filed: Dec. 20, 2004

(86) PCT No.: PCT/JP2004/019028

§ 371 (c)(1),
(2), (4) Date: Jun. 20, 2006

(87) PCT Pub. No.: WO2005/063683

PCT Pub. Date: Jul. 14, 2005

(65) Prior Publication Data

US 2007/0108416 A1    May 17, 2007

(30) Foreign Application Priority Data

Dec. 25, 2003   (JP) ............................. 2003-430490

(51) Int. Cl.
*C09K 15/18*   (2006.01)
*C09K 15/32*   (2006.01)

(52) U.S. Cl. ............................. 252/182.29; 252/400.24; 252/401; 252/389.24; 252/390

(58) Field of Classification Search ............ 252/182.29, 252/400.24
See application file for complete search history.

(56) References Cited

U.S. PATENT DOCUMENTS

| | | | | |
|---|---|---|---|---|
| 6,960,640 | B2 * | 11/2005 | Yoshimura et al. | ............. 528/73 |
| 7,091,307 | B2 * | 8/2006 | Yoshimura et al. | .......... 528/377 |
| 7,169,845 | B2 * | 1/2007 | Tamura et al. | .............. 524/609 |
| 2005/0124711 | A1 * | 6/2005 | Cameron et al. | ............. 521/155 |
| 2007/0108416 | A1 * | 5/2007 | Nagasawa et al. | ............ 252/399 |

FOREIGN PATENT DOCUMENTS

| | | |
|---|---|---|
| JP | 48-61435 | 8/1973 |
| JP | 48061435 | 8/1973 |
| JP | 55-31135 | 8/1980 |
| JP | 02-209851 | 8/1990 |

* cited by examiner

*Primary Examiner*—Joseph D Anthony
(74) *Attorney, Agent, or Firm*—Bacon & Thomas, PLLC

(57) ABSTRACT

A method for inhibiting the discoloration of methylenebisaniline compounds by adding a phosphine of the formula:

$$(H)_p-P-(R^3)_q$$

(wherein $R^3$ is an optionally substituted aryl group or an optionally substituted alkyl group; p is 0, 1 or 2 and q is 1, 2 or 3) to a compound of the formula:

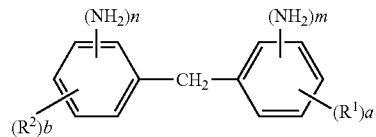

(wherein $R^1$ and $R^2$ are each independently a halogen atom or a C1-C6 alkyl group; a and b are each independently an integer of 0 to 4; m and n are each independently an integer of 1 to 5).

1 Claim, No Drawings

METHOD FOR INHIBITING THE DISCOLORATION OF METHYLENEBISANILINE COMPOUNDS

TECHNICAL FIELD

The present invention relates to a method for inhibiting the discoloration of methylenebisaniline compounds.

BACKGROUND ART

There have been used, as a curing agent for polyurethane/urea, aromatic aniline compounds typified by IHARA CUAMINE MT [a trade name for a product of Ihara Chemical Industry Co. Ltd., commonly known as "MBOCA", 4,4'-methylenebis(2-chloroaniline) (hereinafter, referred to simply as CUAMINE MT)]. When, for example, this CUAMINE MT is actually used, it is melted at one time by the total amount in which it is used on the working day, for reasons of working efficiency and facility, and the melt is gradually used from the start of polyurethane/urea production to the completion of the operation; therefore, part of the melt is kept unused for many hours (about 6 to 13 hours in the production day) and, in some cases, until next morning (until actual use) in the presence of oxygen at temperatures (approximately 120 to 160° C.) which are higher that its melting point (about 100° C.); as a result, CUAMINE MT gives rise to discoloration.

Since discoloration-cause portion in the discolored curing agent or the partial structure thereof remains in the polyurethane/urea produced; therefore, if there is color difference in the curing agent, between the start of operation and the completion of operation, that is, there is discoloration of the curing agent, there is color difference as well in the polyurethane/urea produced between the start of operation and the completion of operation. Therefore, there is no problem when the usage of the polyurethane/urea is not affected by the color thereof; however, when the usage of the polyurethane/urea is affected by the color thereof, the above-mentioned discoloration of the curing agent with the passage of time becomes a major problem which cannot be neglected.

Meanwhile, it was proposed to add, to an aromatic amine, an organic phosphorus compound selected from phosphines, phosphorous acid esters and phosphoric acid esters, to stabilize the aromatic amine. This stabilization includes an aspect of the inhibition of discoloration.

Patent Literature 1: JP-B-1980-31135

This Patent Literature, however, makes no mention as to whether or not the above technique can inhibit the discoloration of methylenebisaniline compounds such as CUAMINE MT and the like when the compounds have been used in such a manner as mentioned above.

DISCLOSURE OF THE INVENTION

Task to be Achieved by the Invention

Thus, it has been desired to develop a method by which the discoloration of methylenebisaniline compounds such as CUAMINE MT and the like can be inhibited even when they have been kept at high temperatures and yet for many hours.

Means for Achieving the Task

In view of the above situation, the present inventor made a study. As a result, it was found that the task can be achieved by adding a phosphine (which has been selected from organic phosphorus compounds) to methylenebisaniline compounds such as CUAMINE MT and the like. The inventor made a further study based on the finding and the present invention has been completed.

The present invention provides a method for inhibiting the discoloration of methylenebisaniline compounds, characterized by adding a phosphine represented by the following general formula:

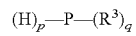

[chemical formula 2]

(wherein $R^3$ is an optionally substituted aryl group or an optionally substituted alkyl group; p is 0, 1 or 2 and q is 1, 2 or 3, with the provisos that the sum of p and q is 3 and that when q is 2 or 3, $R^3$s may be the same or different from each other) to a compound represented by the following general formula:

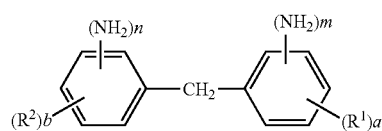

[chemical formula 1]

(wherein $R^1$ and $R^2$ are each independently a halogen atom or a C1-C6 alkyl group; a and b are each independently an integer of 0 to 4; m and n are each independently an integer of 1 to 5, with the provisos that the sum of a and m and the sum of b and n are each 5 or less and that when a is 2 or more, $R^1$s may be the same or different from each other and, when b is 2 or more, $R^2$s may be the same or different from each other).

Effects of the Invention

According to the present invention, the discoloration of methylenebisaniline compounds such as CUAMINE MT and the like can be inhibited even when they have been stored at high temperatures and yet for many hours, by adding thereto a phosphine which has been selected from organic phosphorus compounds.

BEST MODE FOR CARRYING OUT THE INVENTION

The present invention is described in detail below.

The methylenebisaniline compounds which are a target compound in the method of the present invention, are represented by the following formula:

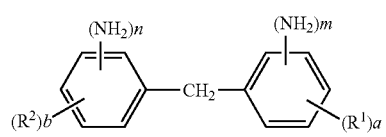

[chemical formula 3]

In the above formula, $R^1$ and $R^2$ are each independently a halogen atom or a C1-C6, straight chain, branched chain or alicyclic alkyl group (C1-C6 alkyl group). Specific examples thereof can include methyl group, ethyl group, n-propyl group, isopropyl group, n-butyl group, sec-butyl group, tert-butyl group, n-pentyl group, n-hexyl group, cyclopropyl group, cyclobutyl group, cyclopentyl group and cyclohexyl group.

a and b are each independently an integer of 0 to 4; and m and n are each independently an integer of 1 to 5. Incidentally, the sum of a and m and the sum of b and n are each 5 or less;

when a is 2 or more, R¹s may be the same or different from each other and, when b is 2 or more, R²s may be the same or different from each other.

Therefore, specific examples of the methylenebisaniline compounds represented by the above formula can include the followings.

4,4'-methylenebisaniline
4,4'-methylenebis(2-chloroaniline)
4,4'-methylenebis(2-ethyl-5-methylaniline)
4,4'-methylenebis(2,3-dichloroaniline)
4,4'-methylenebis(1,3-diaminobenzene)
4,4'-methylenebis(2-chloro-1,3-diaminobenzene)
4,4'-methylenebis(1,2,5-triaminobenzene)
4,4'-methylenebis(2-chloro-1,3,5-triaminobenzene)
4,4'-methylenebis(1,2,3,5-tetraaminobenzene)

Incidentally, in the Patent Literature 1 (JP-B-1980-31135), aromatic amines of broad concept are specified as a target compound; however, only monocyclic compounds are described specifically as the representative compounds or used in the Examples, and compounds such as targeted by the present invention method are not described specifically.

In the method of the present invention, the compound which is added to the compound represented by the above formula and shows a function of inhibiting the discoloration thereof, is a phosphine which has been selected from organic phosphorus compounds. As a specific example of such a compound, there can be mentioned a phosphine represented by the following general formula:

[chemical formula 4]

In the above formula, R³ is an optionally substituted aryl group or an optionally substituted alkyl group. Here, exemplary of the aryl group can be monocyclic or condensed ring aryl groups. Specific examples thereof can be phenyl group, naphthyl group and anthranyl group. Exemplary of the alkyl group can be C1-C8, straight chain, branched chain or alicyclic alkyl groups (C1-C8 alkyl group). Specific examples thereof can be methyl group, ethyl group, n-propyl group, isopropyl group, n-butyl group, sec-butyl group, tert-butyl group, n-pentyl group, n-hexyl group, n-heptyl group, n-octyl group, cyclopropyl group, cyclobutyl group, cyclopentyl group and cyclohexyl group.

As the optional substituents in the above aryl group or in the above alkyl group, there can be mentioned straight chain or branched chain C1-C6 alkyl groups such as methyl group, ethyl group, n-propyl group, isopropyl group, n-butyl group, sec-butyl group, tert-butyl group, n-pentyl group, n-hexyl group and the like; hydroxyl group; straight chain or branched chain C1-C6 alkoxy groups such as methoxy group, ethoxy group, n-propoxy group, isopropoxy group and the like; straight chain or branched chain C1-C6-hydroxyalkyl groups such as hydroxymethyl group, hydroxyethyl group and the like; straight chain or branched chain (C1-C6 alkoxy)-(C1-C6 alkyl) groups such as methoxymethyl group, methoxyethyl group, ethoxyethyl group and the like; straight chain or branched chain C1-C6 haloalkyl groups such as fluoromethyl group, difluoromethyl group, trifluoromethyl group and the like; carboxyl group or metal salts thereof; straight chain or branched chain (C1-C6 alkoxy)carbonyl groups such as methoxycarbonyl group, ethoxycarbonyl group and the like; halogen atoms such as bromine atom, chlorine atom, fluorine atom, iodine atom and the like; nitro group; amino group; straight chain or branched chain mono- or di(C1-C6 alkyl) amino groups such as methylamino group, dimethylamino group, ethylamino group, diethylamino group and the like; straight chain or branched chain (C1-C6 alkyl)carbonylamino groups such as acetylamino group, propionylamino group, butyrylamino group and the like; cyano group; formyl group; straight chain or branched chain (C1-C6 alkyl)carbonyl groups such as methylcarbonyl group, ethylcarbonyl group and the like; and phenyl group [this phenyl group may be substituted with straight chain or branched chain C1-C6 alkyl groups such as methyl group, ethyl group, n-propyl group, isopropyl group, n-butyl group, secbutyl group, tertbutyl group, n-pentyl group, n-hexyl group and the like; hydroxyl group; straight chain or branched chain C1-C6 alkoxy groups such as methoxy group, ethoxy group, n-propoxy group, isopropoxy group and the like; straight chain or branched chain C1-C6-hydroxyalkyl groups such as hydroxymethyl group, hydroxyethyl group and the like; straight chain or branched chain (C1-C6 alkoxy)-(C1-C6 alkyl) groups such as methoxymethyl group, methoxyethyl group, ethoxyethyl group and the like; straight chain or branched chain C1-C6 haloalkyl groups such as fluoromethyl group, difluoromethyl group, trifluoromethyl group and the like; carboxyl group or metal salts thereof; straight chain or branched chain (C1-C6 alkoxy)carbonyl groups such as methoxycarbonyl group, ethoxycarbonyl group and the like; halogen atoms such as bromine atom, chlorine atom, fluorine atom, iodine atom and the like; nitro group; amino group; straight chain or branched chain mono- or di(C1-C6 alkyl) amino groups such as methylamino group, dimethylamino group, ethylamino group, diethylamino group and the like; straight chain or branched chain (C1-C6 alkyl)carbonylamino groups such as acetylamino group, propionylamino group, butyrylamino group and the like; cyano group; formyl group; straight chain or branched chain (C1-C6 alkyl)carbonyl groups such as methylcarbonyl group, ethylcarbonyl group and the like; etc.].

Incidentally, p is 0, 1 or 2 and q is 1, 2 or 3 with the provisos that the sum of p and q is 3 and that, when q is 2 or 3, R³s may be the same or different from each other.

Therefore, as specific examples of the phosphine represented by the above formula, there can be mentioned:

(1) mono-substituted phosphines typified by monoalkyl- or monoarylphosphines, such as ethylphosphine [(H)₂—P-Et], n-butylphosphine [(H)₂—P-(n-Bu)], phenylphosphine [(H)₂—P-Ph] and the like;

(2) di-substituted phosphines typified by dialkyl- or diarylphosphines, such as diethylphosphine [H—P-(Et)₂], di(n-butyl)phosphine [H—P-(n-Bu)₂], diphenylphosphine [H—P-(Ph)₂] and the like; and (3) tri-substituted phosphines typified by trialkyl- or triarylphosphines, such as triethylphosphine [P-(Et)₃], tri(n-butyl)phosphine [P-(n-Bu)₃], tri(cyclohexyl)phosphine [P-(c-Hex)₃], triphenylphosphine (TPP) [P-(Ph)₃] and the like.

Of the phosphines represented by the above general formula, a tri-substituted phosphine is preferred, a triarylphosphine is more preferred, and triphenylphosphine (TPP) is particularly preferred.

The amount of the phosphine added to the methylenebisaniline compound represented by the above formula is, for example, 100 to 20,000 ppm, preferably 500 to 5,000 ppm.

In the Patent Literature 1 (JP-B-1980-31135) is described addition, to an aromatic amine, of an organic phosphorus compound selected from phosphines, phosphorous acid esters and phosphoric acid esters; the phosphines, phosphorous acid esters and phosphoric acid esters all as organic phosphorus compounds, are regarded equally; and there is no description as to the combination use of a particular compound (which is a target compound of the present invention) and a phosphine or to the effect of such combination use.

As described above, when the methylenebisaniline compound (typified by CUAMINE MT) represented by the above-shown formula is actually used as a curing agent for polyurethane/urea, part of the compound is kept unused in a molten state for many hours (about 6 to 13 hours in the production day) in the presence of oxygen at temperatures (approximately 120 to 160° C.) which are higher that its melting point (about 100° C.). The discoloration of the methylenebisaniline compound can be inhibited even when the compound has been kept under the above conditions, by adding a phosphine to the methylenebisaniline compound according to the present invention.

In the Patent Literature 1 (JP-B-1980-31135), there is confirmed a stabilization effect in a short period of 100 minutes; however, there is no verification as to the effect under the conditions of high temperatures and many hours, such as mentioned above.

In carrying out the present invention, a phosphine may be simply added to the compound represented by the above-shown formula. As necessary, additives such as ultraviolet absorber, oxidation inhibitor, light stabilizer [HALS (hindered amine light stabilizer)] and the like may be used in combination.

EXAMPLES

Next, the production method of the present invention compound is specifically described by way of Examples. However, the present invention is in no way restricted by these Examples.

In the following Examples and Comparative Examples, the generation and degree of discoloration of methylenebisaniline compound were examined using a calorimeter CT-310 (a product of MINOLTA CO., LTD.) and employing the L*a*b* trichromatic system used in JIS Z 8729. In this system, color is expressed by coordinates of three-dimensional color space of L* value, a* value and b* value. Here, the L* value indicates a lightness expressed in a range of 0 to 100; as the L* value is larger, the color becomes brighter (more white) and, as the L* value is smaller, the color becomes darker (more black). The a* value and the b* value indicate a chromaticity (a hue and a saturation) in combination. The a* value is in a range from −100 to +100; as the a* value is larger, the color becomes more red and, as the a* value is smaller, the color becomes more green. The b* value is also in a range of −100 to +100; as the b* value is larger, the color becomes more yellow and, as the b* value is smaller, the color becomes more blue.

Example 1

1,000 ppm of triphenylphosphine was added to a compound represented by the following formula:

[chemical formula 5]

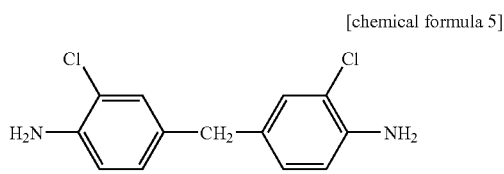

The mixture was allowed to stand at 160° C. for 13 hours. The discoloration of the compound represented by the above formula before and after heating were measured and expressed by L* value and a* value. The L* value changed from 93.96 to 89.54 and the a* value changed from −8.66 to −3.31. In a visual inspection at the completion of the test, the light yellow color at the start of heating remained and there was no significant discoloration.

Comparative Example 1

The discoloration of the compound represented by the above formula before and after heating were measured in the same manner as in Example 1 except that the triphenylphosphine was changed to tri(nonylphenyl) phosphite, and expressed by L* value and a* value. The L* value changed from 91.02 to 53.45 and the a* value changed from −2.71 to +44.85. In a visual inspection at the completion of the test, the light yellow color at the start of heating changed to reddish brown color and there was significant discoloration.

Example 2

1,000 ppm of tri(n-butyl)phosphine was added to the compound represented by the above formula. The mixture was allowed to stand at 160° C. for 6 hours. The discoloration of the compound represented by the above formula after heating was measured and expressed by L* value and a* value. The L* value was 77.86 and the a* value was −11.73. In a visual inspection at the completion of the test, the light yellow color at the start of heating remained and there was no significant discoloration.

Example 3

Heating was conducted in the same manner as in Example 2 except that the amount of tri(n-butyl)phosphine added was changed to 3,000 ppm. The discoloration of the compound after heating was measured and expressed by L* value and a* value. The L* value was 81.13 and the a* value was −12.64. In a visual inspection at the completion of the test, the light yellow color at the start of heating remained and there was no significant discoloration.

Example 4

Heating was conducted in the same manner as in Example 2 except that the amount of tri(n-butyl)phosphine added was changed to 5,000 ppm. The discoloration of the compound after heating was measured and expressed by L* value and a* value. The L* value was 77.14 and the a* value was −12.84. In a visual inspection at the completion of the test, the light yellow color at the start of heating remained and there was no significant discoloration.

Comparative Example 2

1,000 ppm of tri(n-butyl) phosphite was added to the compound represented by the above formula. The mixture was allowed to stand at 160° C. for 6 hours. The discoloration of the compound represented by the above formula after heating was measured and expressed by L* value and a* value. The L* value was 69.96 and the a* value was 0.77. In a visual inspection at the completion of the test, the light yellow color at the start of heating changed reddish brown color and there was significant discoloration.

Comparative Example 3

Heating was conducted in the same manner as in Comparative Example 2 except that the amount of tri(n-butyl) phosphite added was changed to 3,000 ppm. The discoloration of the compound after heating was measured and expressed by L* value and a* value. The L* value was 68.23 and the a* value was 3.24. In a visual inspection at the completion of the test, the light yellow color at the start of heating changed to reddish brown color and there was significant discoloration.

Comparative Example 4

Heating was conducted in the same manner as in Comparative Example 2 except that the amount of tri(n-butyl) phosphite added was changed to 5,000 ppm. The discoloration of the compound after heating was measured and expressed by L* value and a* value. The L* value was 68.7 and the a* value was 2.93. In a visual inspection at the completion of the test, the light yellow color at the start of heating changed to reddish brown color and there was significant discoloration.

Example 5

1,000 ppm of tri(cyclohexyl)phosphine was added to the compound represented by the above formula. The mixture was allowed to stand at 160° C. for 6 hours. The discoloration of the compound represented by the above formula after heating was measured and expressed by L* value and a* value. The L* value was 74.78 and the a* value was −8.19. In a visual inspection at the completion of the test, the light yellow color at the start of heating remained and there was no significant discoloration.

Example 6

Heating was conducted in the same manner as in Example 5 except that the amount of tri(cyclohexyl)phosphine added was changed to 3,000 ppm. The discoloration of the compound after heating was measured and expressed by L* value and a* value. The L* value was 73.35 and the a* value was −8.33. In a visual inspection at the completion of the test, the light yellow color at the start of heating remained and there was no significant discoloration.

Example 7

Heating was conducted in the same manner as in Example 5 except that the amount of tri(cyclohexyl)phosphine added was changed to 5,000 ppm. The discoloration of the compound after heating was measured and expressed by L* value and a* value. The L* value was 76.05 and the a* value was −8.76. In a visual inspection at the completion of the test, the light yellow color at the start of heating remained and there was no significant discoloration.

Comparative Example 5

1,000 ppm of tri(isodecyl) phosphite was added to the compound represented by the above formula. The mixture was allowed to stand at 160° C. for 6 hours. The discoloration of the compound represented by the above formula after heating was measured and expressed by L* value and a* value. The L* value was 62.47 and the a* value was 4.80. In a visual inspection at the completion of the test, the light yellow color at the start of heating changed to reddish brown color and there was significant discoloration.

Comparative Example 6

Heating was conducted in the same manner as in Comparative Example 5 except that the amount of tri(isodecyl) phosphite added was changed to 3,000 ppm. The discoloration of the compound after heating was measured and expressed by L* value and a* value. The L* value was 59.24 and the a* value was 5.60. In a visual inspection at the completion of the test, the light yellow color at the start of heating changed to reddish brown color and there was significant discoloration.

Comparative Example 7

Heating was conducted in the same manner as in Comparative Example 5 except that the amount of tri(n-butyl) phosphite added was changed to 5,000 ppm. The discoloration of the compound after heating was measured and expressed by L* value and a* value. The L* value was 61.51 and the a* value was 5.39. In a visual inspection at the completion of the test, the light yellow color at the start of heating changed to reddish brown color and there was significant discoloration.

As seen above, in each of Examples 1 to 7 wherein a phosphine was added to the methylenebisaniline compound represented by the above formula, the L* value was kept at a high level and the a* value was kept at a low level during the heating and the discoloration was extremely low. In contrast, in each of Comparative Examples 1 to 7 wherein a phosphite was added to the methylenebisaniline compound represented by the above formula, there were a large decrease in L* value and a large increase in a* value and there was significant discoloration.

INDUSTRIAL APPLICABILITY

According to the method of the present invention, the discoloration of particular methylenebisaniline compounds such as Cuamine MT and the like can be inhibited even when the methylenebisaniline compounds have been stored at high temperatures and yet for many hours, by adding thereto a phosphine selected from organic phosphorus compounds.

The invention claimed is:

1. A method for inhibiting the discoloration of methylenebisaniline compounds, characterized by adding a phosphine represented by the following general formula:

[chemical formula 2]

(wherein $R^3$ is an optionally substituted aryl group or an optionally substituted alkyl group; p is 0, 1 or 2 and q is 1, 2 or 3, with the provisos that the sum of p and q is 3 and that when q is 2 or 3, $R^3$ may be the same or different from each other) to a compound represented by the following general formula:

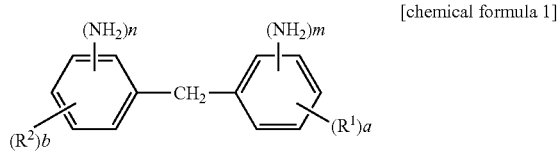

[chemical formula 1]

(wherein $R^1$ and $R^2$ are each independently a halogen atom or a C1-C6 alkyl group; a and b are each independently an integer of 0 to 4; m and n are each independently an integer of 1 to 5, with the provisos that the sum of a and m and the sum of b and n are each 5 or less and that when a is 2 or more, $R^1$ may be the same or different from each other and, when b is 2 or more, $R^2$ may be the same or different from each other).

* * * * *

UNITED STATES PATENT AND TRADEMARK OFFICE
CERTIFICATE OF CORRECTION

PATENT NO. : 7,632,424 B2
APPLICATION NO. : 10/583722
DATED : December 15, 2009
INVENTOR(S) : Nagasawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 841 days.

Signed and Sealed this

Twenty-first Day of December, 2010

David J. Kappos
*Director of the United States Patent and Trademark Office*